United States Patent [19]

O'Leary

[11] Patent Number: 4,794,917
[45] Date of Patent: Jan. 3, 1989

[54] CERVICAL SUPPORT

[76] Inventor: John O'Leary, 14322 Wallace, Harvey, Ill. 60426

[21] Appl. No.: 55,365

[22] Filed: May 29, 1987

[51] Int. Cl.⁴ .............................................. A61F 5/04
[52] U.S. Cl. .................................................. 128/87 B
[58] Field of Search ...................... 128/87 B, 87 R, 88

[56] References Cited

U.S. PATENT DOCUMENTS

| | | | |
|---|---|---|---|
| 3,795,243 | 3/1974 | Miller | 128/87 B |
| 4,034,748 | 7/1977 | Winner | 128/87 R |
| 4,141,368 | 2/1979 | Meyer | 128/87 B |
| 4,211,218 | 7/1980 | Kendrick | 128/87 R |
| 4,252,113 | 2/1981 | Scire | 128/87 R |
| 4,299,209 | 10/1981 | Behrens et al. | 128/87 B |
| 4,665,908 | 5/1987 | Calkin | 128/88 |

Primary Examiner—Robert A. Hafer
Assistant Examiner—Michael Brown
Attorney, Agent, or Firm—Jones, Day, Reavis & Pogue

[57] ABSTRACT

A cervical support for use in immobilizing victims of spinal injuries and particularly for use in immobilizing vehical crash victims prior to their extrication from the vehicle. The cervical support includes a cervical splint dimensioned to extend from the top of the head to about midback of an adult victim, and which is shaped to follow the outline of the victim's head and shoulders. The cervical support is provided with head and chest straps for securing the victim to the splint. The head straps wrap about the forehead and the chin of the victim, and the chest straps extend over the shoulder and under the opposite arm in criss-cross fashion across the chest. The strap arrangement permits diagnosis and treatment of other injuries while keeping the victim immobilized.

3 Claims, 2 Drawing Sheets

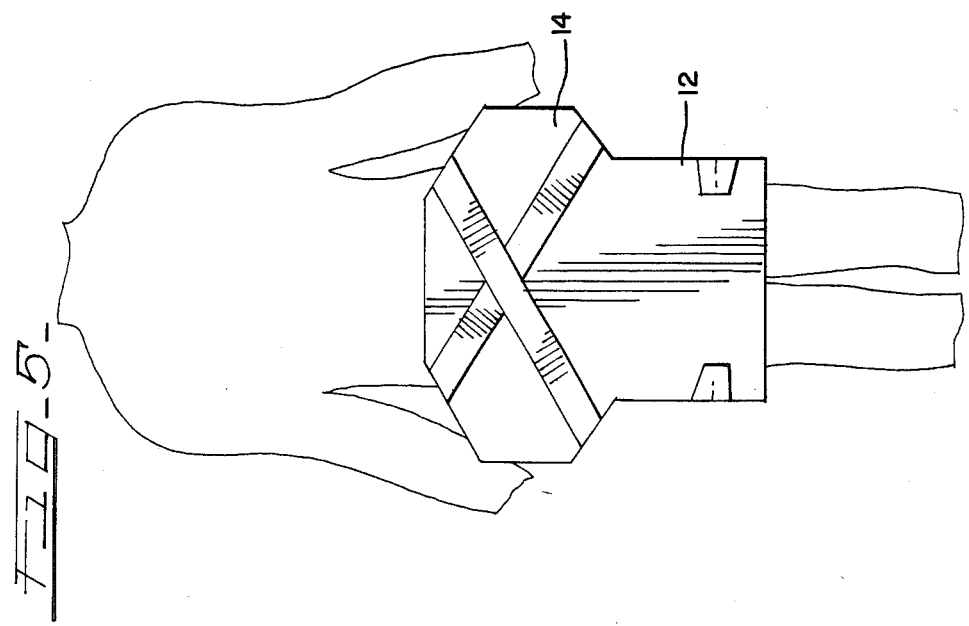
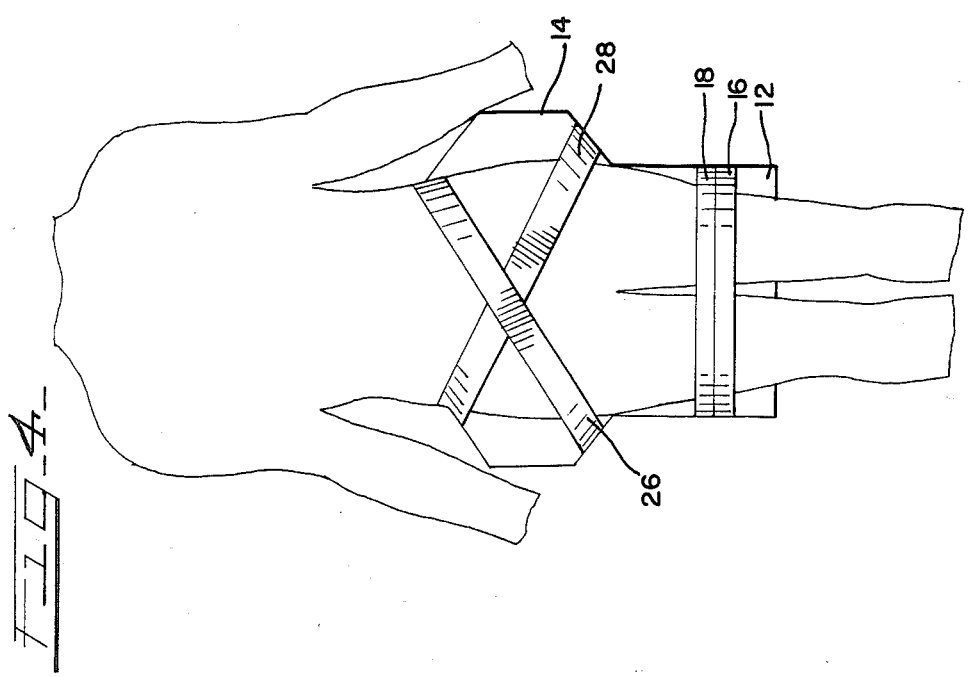

CERVICAL SUPPORT

BACKGROUND OF THE INVENTION

The present invention relates to a cervical spinal immobilization device and, more particularly, to a device particularly adapted for use with emergency medical victims to immobilize the victim prior to extrication from, for example, a motor vehicle.

Because of recent interest in the emergency medical care field, new standards have been established for the proper prehospital handling of trauma patients in order to improve the patient's chances for recovery. Such proper handling requires rapid extrication of the patient from the accident situation and immediate transport to a medical facility for treatment. If a neck or spinal injury is suspected, the patient must be completely immobilized before extrication in order to reduce the severity of the injury and minimize the danger of paralysis.

Several spinal immobilization devices have been developed. Generally, these devices comprise short or long spine boards which are used in association with other devices such as cervical collars, body harnesses or straps.

One example of a short spine board is disclosed in U.S. Pat. No. 4,299,209 to Behrens et al. This device comprises an arcuately formed board which is shaped to conform with the human body. The board is contoured into portions which approximately outline the patient's head, shoulders, and main body, with the length of the main body portion being sufficient to support the entire torso of the patient. The board is also designed so that a cervical collar may be used in association with the board to provide immobilization when a neck injury is indicated.

Another short spine board is disclosed in U.S. Pat. No. 4,034,748 to Winner. This device comprises a board which extends from the head to the crotch of the patient and includes an inflatable head immobilizer which is placed against the sides of the head and secured thereto by a head strap. The device is further provided with chest and crotch straps to secure the patient to the board for transport.

U.S. Pat. No. 4,143,654 to Sherman discloses a short spine board system comprising in combination a short spine board and a body vest. The spine board extends upward from the base of the patient's spine and fits inside a pocket formed in the vest. The vest is provided with shoulder and waist straps which wrap around the patient to form the vest.

U.S. Pat. No. 4,024,861 to Vincent discloses an inflatable spinal support having head and body straps which secure a patient to the support to immobilize the patient's spine during transport. The spinal support generally extends from the top of the head to the base of the patient's spine, but may be of a length greater than the height of the patient.

Another spinal support device is disclosed in U.S. Pat. No. 3,724,453 to Dixon et al. This device comprises a splint board which extends from the bottom of the spine to the head of the patient. The board is provided with head and body harnesses which hold the patient's head and torso in position against the splint.

Previous spinal supports suffer from several disadvantages. These supports generally extend from the patient's head to the base of the spine or longer, making them difficult to use when the patient is in a tightly confined area, such as a crushed vehicle. Also, many of the spinal supports are designed to be used in conjunction with a cervical collar when neck injuries are indicated. Such cervical collars, it has been shown, do not effectively immobilize the head and neck. In addition, the use of a cervical collar prevents access to the major arteries and veins in the neck, and must be removed if a tracheotomy must be performed.

Another disadvantage of prior art spinal supports is that they often employ only a single head strap and a single body strap. This limited number of straps may not be enough to effectively immobilize the patient. Further, treatment of other injuries to the head or body may be necessary which would require loosening or undoing the strap during treatment. When only two straps are employed, removal of one of the straps to permit additional treatment invites substantial risk of patient movement, leading to increased damage to the spinal cord.

It is therefore an object of the invention to provide a cervical support device which is shorter than prior art spinal boards and thus easier to maneuver, even in confined situations. The device of the present invention generally extends from the top of the head to the mid-back of an average-sized adult patient rather than to the base of the spine or crotch as in prior art devices. It is further an object of the present invention to provide a cervical support which substantially completely immobilizes the head and neck region of a patient without the need for a cervical collar.

Another object of the present invention is to provide a cervical support which provides effective immobilization of the patient while still permitting treatment of other injuries the patient may have suffered. A further object of the present invention is to provide a cervical support which may be used with patients of varying size without alternations or modifications in the support.

These and other objects and advantages of the present invention will become apparent from the following description.

SUMMARY OF THE INVENTION

In general, the cervical support of the present invention comprises a cervical splint which is contoured to approximate the head and upper back of a patient. The upper back portion of the splint is preferably octagonal and approximately follows the outline of the trapezius muscle in the patient's neck and upper back. This design helps to restrict movement of the neck, shoulders and upper back, thus keeping the spine aligned to prevent further injury. The octagonal shape also facilitates proper shoulder strap alignment by providing angled sides which approximate the outline of the patient's shoulders. Further, since the bottom of the upper back portion is tapered, the cervical splint is easier to maneuver behind a patient than prior art splints. The head portion of the splint is approximately rectangular and is wide enough to permit bulk dressings to be placed on either side of the patient's head to further restrict head movement.

The cervical splint is shorter than the standard short spine board, being about twenty two inches in length and extending from the top of the head to about the patient's mid-back. The short length combined with the tapered bottom of the splint permits greater maneuverability in tight, confined situations, allowing quick immobilization without major manipulation or movement of the patient.

The cervical support further comprises head and chest straps for securing the patient to the cervical splint. The head straps wrap transversely around the patient's forehead and chin. The double strap arrangement substantially completely eliminates any side to side and up and down movement of the head while still permitting movement of the jaw so that the patient's mouth may be opened.

Each of the chest straps extends over a shoulder and under the opposite arm to meet in criss-cross fashion across the chest to secure the upper back and shoulders to the splint. The chest strap arrangement leaves the chest area open for diagnosis and, if necessary, emergency treatment of other injuries.

DESCRIPTION OF THE DRAWINGS

FIG. 4 is a front view showing the use of the present invention as a pelvic support on a patient.

FIG. 5 is a rear view showing the use of the present invention as a pelvic support on a patient.

DETAILED DESCRIPTION OF THE INVENTION

Figure 1:
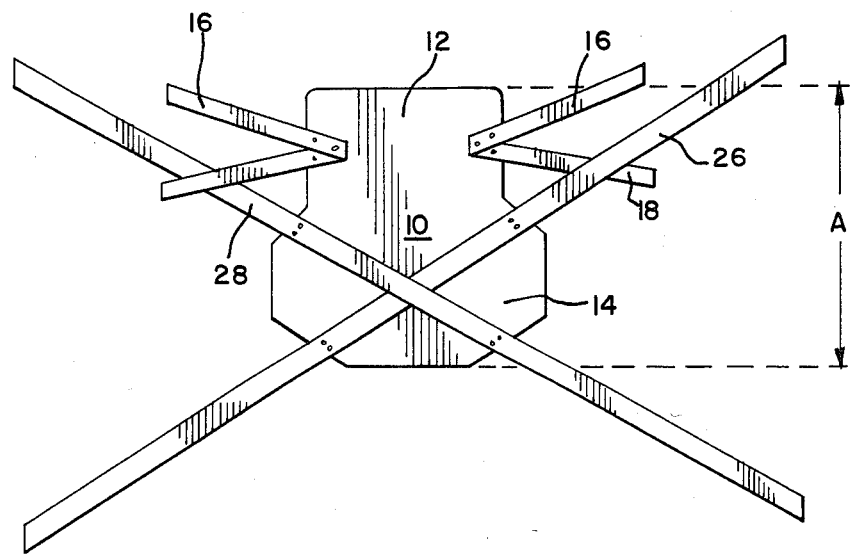
FIG. 1 is a perspective view illustrating the cervical support board of the present invention.

Referring now to FIG. 1, the cervical support device of the present invention comprises a rigid, thin cervical splint 10, having a head portion 12 and an upper back portion 14. The length of the splint 10 as shown at A is approximately twenty-two inches, the splint extending from the top of the head to about the mid-back of the patient. The thickness of the splint 10 is preferably about ⅛ inch. The ⅛ inch thickness allows the splint to be used in conjunction with a long spinal board or other such carrier for transporting a patient to a hospital.

The splint 10 may be made of various light-weight rigid materials, for example fiberglass, reinforced plastic, wood or metal. Preferably, the splint 10 is made of a material transparent to x-rays to allow the patient to be x-rayed without removing the cervical support device. The splint 10 may also be coated with a blood resistant coating, such as polyurethane, so that the splint can be easily cleaned.

Figure 2:
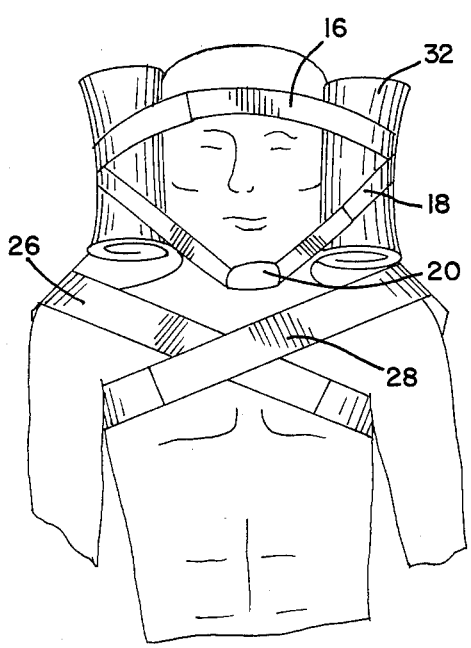
FIG. 2 is a perspective view showing the use of the cervical support of the present invention on a patient.

The head portion 12 is generally rectangular and is of sufficient width to allow bulk dressings such as rolled towels or blankets to be secured on either side of the patient's head, as shown in FIG. 2. Generally, the head portion 12 will be about sixteen inches wide. The upper back portion 14 is octagonal and approximately follows the outline of the trapezius muscle in the patient's neck and upper back. The octagonal shape provides maximum support for the patient's upper back and shoulders and helps to restrict movement of the neck, shoulders and upper back, thus keeping the spine aligned to prevent further injury.

The head portion 12 is provided with head straps 16 and chin straps 18 for securing a patient's head to the splint 10. One end of each head and chin strap is mounted to the back of the head portion 12 by any suitable means, such as tacks or rivets. The other ends of the head and chin straps 16 and 18 are provided with fastening means, such as complementary elements of "Velcro" material. As is well known, one element of such material consists of hook-like nylon pile fabric and the other consists of nylon pile material. The two elements adhere to each other when pressed together but may be readily separated. Preferably, the entire lengths of the head and chin straps 16 and 18 are provided with Velcro material to allow for variations in head size and to permit the use of bulk dressings 32, shown in FIG. 2, if necessary. The chin strap 18 may be provided with a chin cup 20, as best shown in FIG. 2, to help minimize head movement. The chin cup 20 is slidable across the chin strap 18 to adjust for variations in head size. Although head straps 16 and 18 are shown as pairs of strap elements, it will be appreciated that the straps 16 and 18 may each be formed from a single strip continuous from end to end.

The upper back portion 14 is provided with chest straps 26 and 28 for securing the patient's upper body to the splint 10. The chest straps are mounted to the back of the upper back portion 14 by any suitable means. To insure proper strap alignment when the splint is in use, it is preferable to afix the straps 26 and 28 at the angled sides of the upper back portion 14, as shown in FIG. 1. The chest straps 26 and 28 are provided with fastening means, such as the complementary elements of Velcro discussed previously. The chest straps 26 and 28 may consist of individual strap elements mounted to the splint 10, or preferably each strap may be formed from a single strip continuous from end to end, as shown in FIG. 1.

Figure 3:
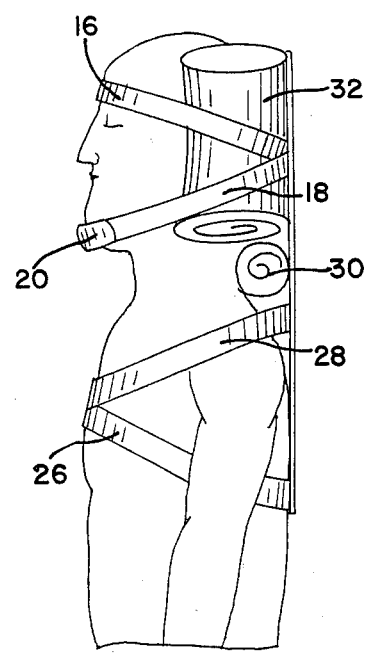
FIG. 3 is a side view showing the use of the cervical support on a patient.

FIGS. 2 and 3 illustrate the manner in which the cervical support of the present invention can be used with a patient. The cervical splint 10 is slipped behind the head and upper back of a patient and a bulk dressing 30 is placed behind the neck to maintain the head in a neutral position. Additional bulk dressings 32 are placed on either side of the patient's head to limit head movement and are held in place by head and chin straps 16 and 18.

The ends of the head straps 16 are brought together around the bulk dressings 32 and fastened about the patient's forehead to secure the top of the head to the splint 10 and hold the bulk dressings 32 in place. The ends of the chin straps 18 are similarly brought together around the bulk dressings and fastened about the patient's chin. The chin straps 18 are arranged and fastened so that the patient's chin rests in the chin cup 20. With this arrangement, the chin straps 18 can move with the mandible or lower jaw to ensure that the patient's air passage remains open. This is an important consideration since the air passage must be kept open to prevent aspiration in the event of vomiting.

Once the head and chin straps are fastened, the patient's head is substantially completely immobilized. As will be appreciated, the head and chin straps 16 and 18 eliminate the need for a cervical collar and leave the neck area exposed in the event that further treatment, such as a tracheotomy, must be performed.

The chest straps 26 and 28 extend over the patient's shoulders and under the opposite arms and are fastened in criss-cross fashion as illustrated in FIG. 2. The chest strap arrangement holds the upper body and splint in a rigid line by the use of equal and opposite pressure, and substantially completely immobilizes the patient. Further, the chest area remains exposed with this arrangement, permitting diagnosis and treatment of other injuries.

The cervical support may also be used when a patient has suffered a pelvic or hip fracture or dislocation. When used in this manner, the splint 10 is turned around so that the upper back portion 14 is secured to the patient's hips and the head portion 12 is secured to the legs. The chest straps 26 and 28 secure the hips to the splint 10 in criss-cross fashion and the head and chin straps 16 and 18 wrap around and secure the thighs.

One of the advantages of this invention over the prior art is that it may be used with patients of varying size, from a child to an adult, without making adjustments in the straps or the length of the splint. This faciliatates rapid application to a patient in an emergency situation without wasting precious time to adjust for size.

A further advantage of this invention is that it may be used to immobilize a patient without first aligning the patient's head. In cases where an attempt to align the head results in increased pain or muscle spasm, the head should be immobilized in the position in which it is found. This may be accomplished with the present invention by padding the head with additional bulk dressings and securing with the head and chin straps.

The cervical support of the invention is also light, extremely portable and easily applied because of its smaller size. In most situations only two people are needed to apply the device, rather than the three or more people typically required for prior art devices.

It will be understood that various changes and modifications may be made in the details of the invention without departing from the spirit thereof, particularly as defined by the following claims:

That which is claimed is:

1. A dual purpose cervical and pelvic support for the upper body and head or pelvis and hip of an injured person comprising:
   (a) a planar rigid splint including a rectangular top portion and an octagonal base portion said base portion being of sufficient size to extend from the shoulders to the mid-back of the person to thereby correspond to the outline of the person's trapezious muscle and said top portion extending from said body portion and terminating at the top of the head of the person;
   (b) a plurality of straps mounted to the top portion of said splint, selected ones of said straps being of sufficient length to be secured transversely about the forehead or thighs of the person and selected other ones of said straps being arranged to extending along the jawline of the person's chin to hold the head of the person in position against the splint to stabilize the head relative to the chest without applying traction thereto;
   (c) a pair of strap members mounted to the base portion of said splint including means for allowing infinite adjustable connection with one another, said strap members being of a length sufficient to cross one another in the center of the upper body or pelvic area of the person and extending beyond the edges of the upper body or pelvic area such that said strap members can be secured over a shoulder and under the opposite arm of the person to secure the upper body and shoulders of the person against the splint or can be secured across the hip and pelvic area of the person to secure the pelvic area of the person to the splint.

2. A cervical support according to claim 1, wherein the splint is about twenty-two inches in length.

3. A cervical support according to claim 1, wherein one of said head straps is provided with a chin cup for receiving the chin of the patient.

* * * * *